(12) United States Patent
Yasunaga

(10) Patent No.: US 9,833,278 B2
(45) Date of Patent: Dec. 5, 2017

(54) MEDICAL TREATMENT APPARATUS AND METHOD OF CONTROLLING THE SAME

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

(*) Notice: Subject to any disclaimer, the term of this patent is extended or adjusted under 35 U.S.C. 154(b) by 1241 days.

(21) Appl. No.: 13/893,695

(22) Filed: May 14, 2013

(65) Prior Publication Data

US 2013/0245619 A1    Sep. 19, 2013

Related U.S. Application Data

(63) Continuation of application No. PCT/JP2011/078542, filed on Dec. 9, 2011.

(30) Foreign Application Priority Data

Dec. 14, 2010 (JP) ................. 2010-278062

(51) Int. Cl.
*A61B 18/08* (2006.01)
*A61B 18/14* (2006.01)
*A61B 18/00* (2006.01)

(52) U.S. Cl.
CPC .......... *A61B 18/082* (2013.01); *A61B 18/085* (2013.01); *A61B 18/1445* (2013.01);
(Continued)

(58) Field of Classification Search
CPC ................ A61B 18/082; A61B 18/085; A61B 2018/00589; A61B 2018/00595;
(Continued)

(56) References Cited

U.S. PATENT DOCUMENTS

2004/0092923 A1* 5/2004 Miura ................. A61B 18/085
606/28
2005/0021017 A1  1/2005 Karasawa et al.

FOREIGN PATENT DOCUMENTS

EP    1 582 165 A1    10/2005
EP    1 829 493 A1    9/2007
(Continued)

OTHER PUBLICATIONS

Extended Supplementary European Search report dated Dec. 16, 2014 from related European Application No. 11 84 9199.2.
(Continued)

*Primary Examiner* — Joseph Stoklosa
*Assistant Examiner* — Tigist Demie
(74) *Attorney, Agent, or Firm* — Scully, Scott, Murphy & Presser, P.C.

(57) ABSTRACT

A medical treatment apparatus includes a heat transfer portion, a heating chip, a temperature measurement unit and a control unit. The heat transfer portion comes into contact with a living tissue and transfers heat to the living tissue. The heating chip includes a heating region, is joined to the heat transfer portion, and heats the heat transfer portion by inputting energy to the heating region. The temperature measurement unit acquires a temperature of the heating region. The control unit controls a temperature of the heat transfer portion to a target temperature by controlling the temperature of the heating region to a temperature differing from the target temperature by an offset value which changes in accordance with an amount of the energy.

5 Claims, 16 Drawing Sheets

(52) U.S. Cl.
CPC ............... *A61B 2018/00589* (2013.01); *A61B 2018/00595* (2013.01); *A61B 2018/00601* (2013.01); *A61B 2018/00791* (2013.01); *A61B 2018/1455* (2013.01)

(58) Field of Classification Search
CPC  A61B 2018/00601; A61B 2018/00791; A61B 2018/1455
See application file for complete search history.

(56) References Cited

FOREIGN PATENT DOCUMENTS

| | | |
|---|---|---|
| EP | 2 106 762 A1 | 10/2009 |
| JP | 2003-208964 A | 7/2003 |
| JP | 2005-110713 A | 4/2005 |
| JP | 2007-037845 A | 2/2007 |
| JP | 2009-247893 A | 10/2009 |

OTHER PUBLICATIONS

International Search Report dated Feb. 21, 2012 issued in PCT/JP2011/078542 together with an English language translation.
International Preliminary Report on Patentability together with the Written Opinion dated Jun. 27, 2013 received in related International Application No. PCT/JP2011/078542.

\* cited by examiner

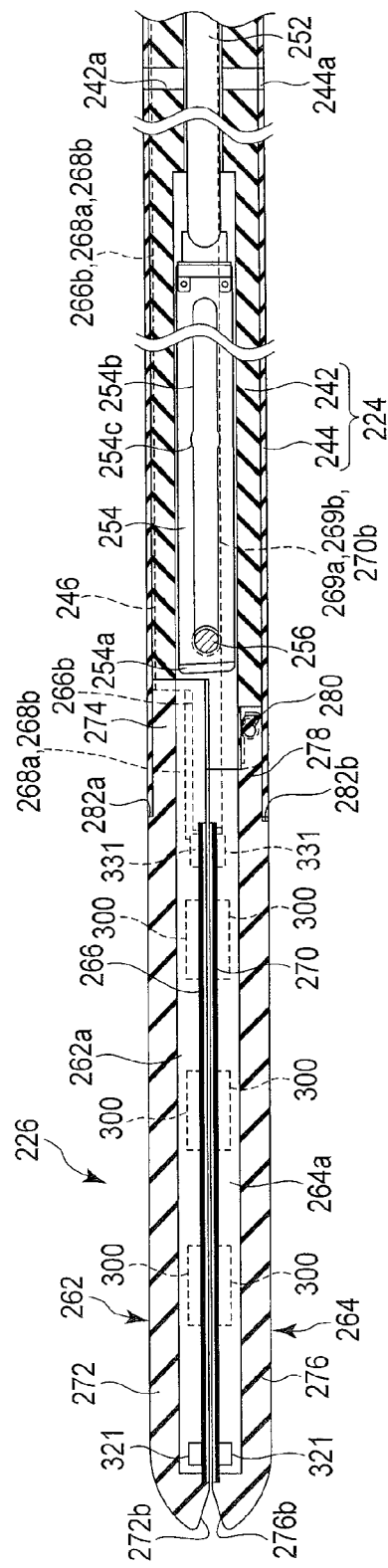
F I G. 2A

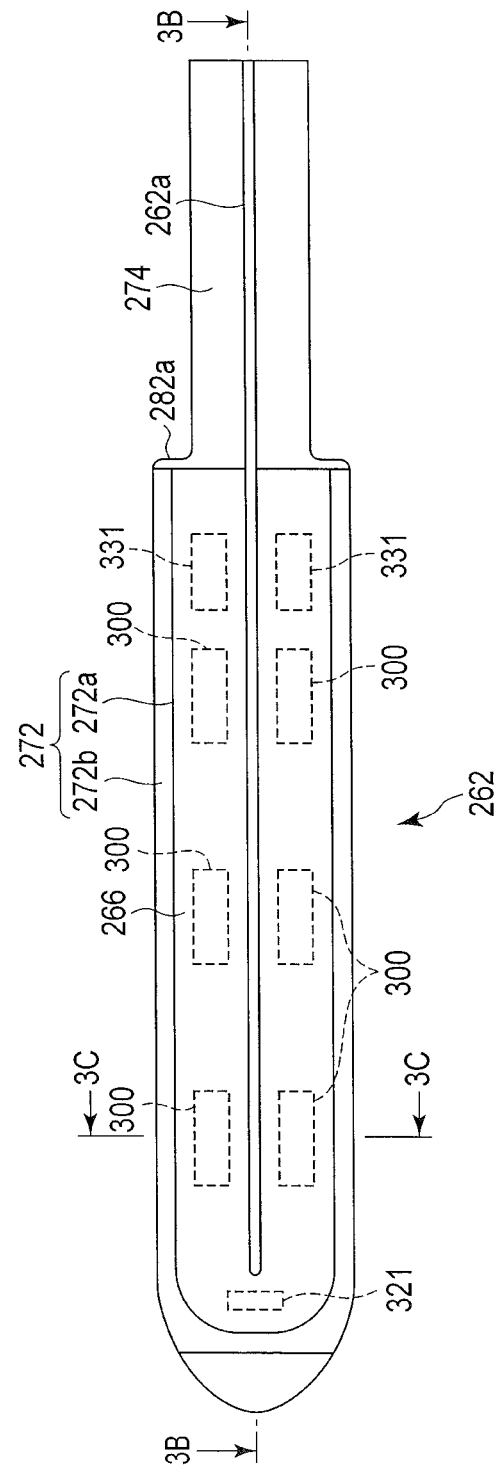
F I G. 3A

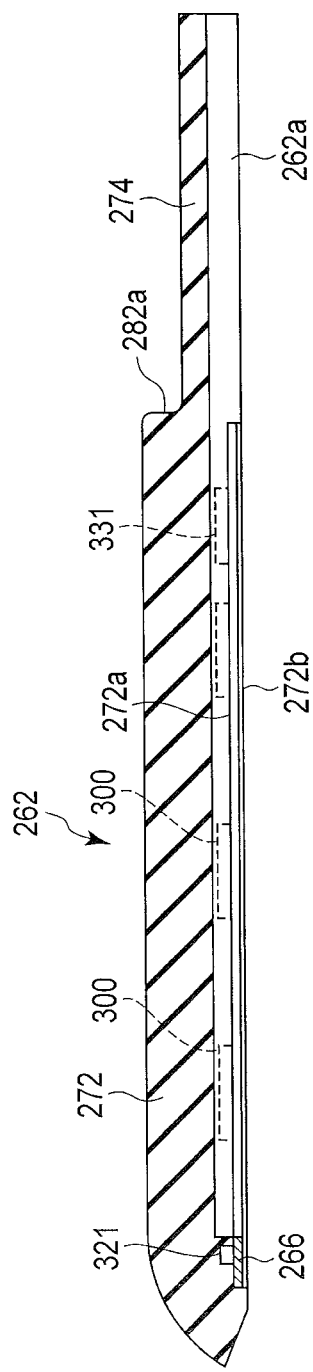
F I G. 3B

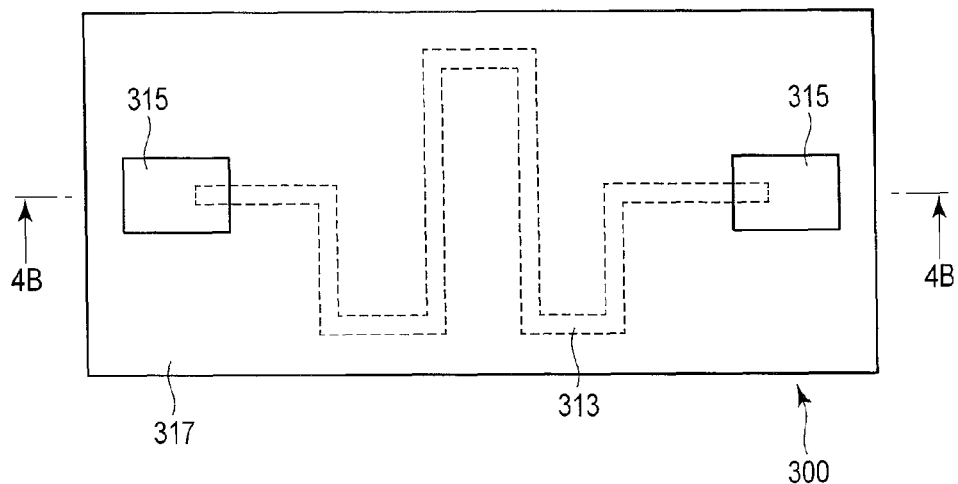
F I G. 4A
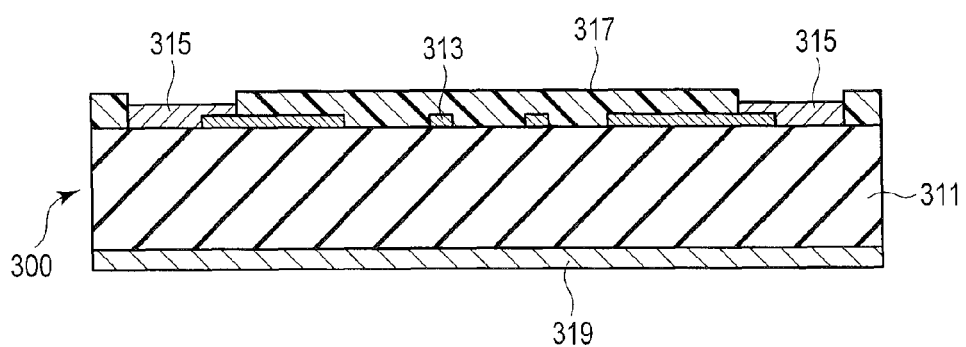
F I G. 4B

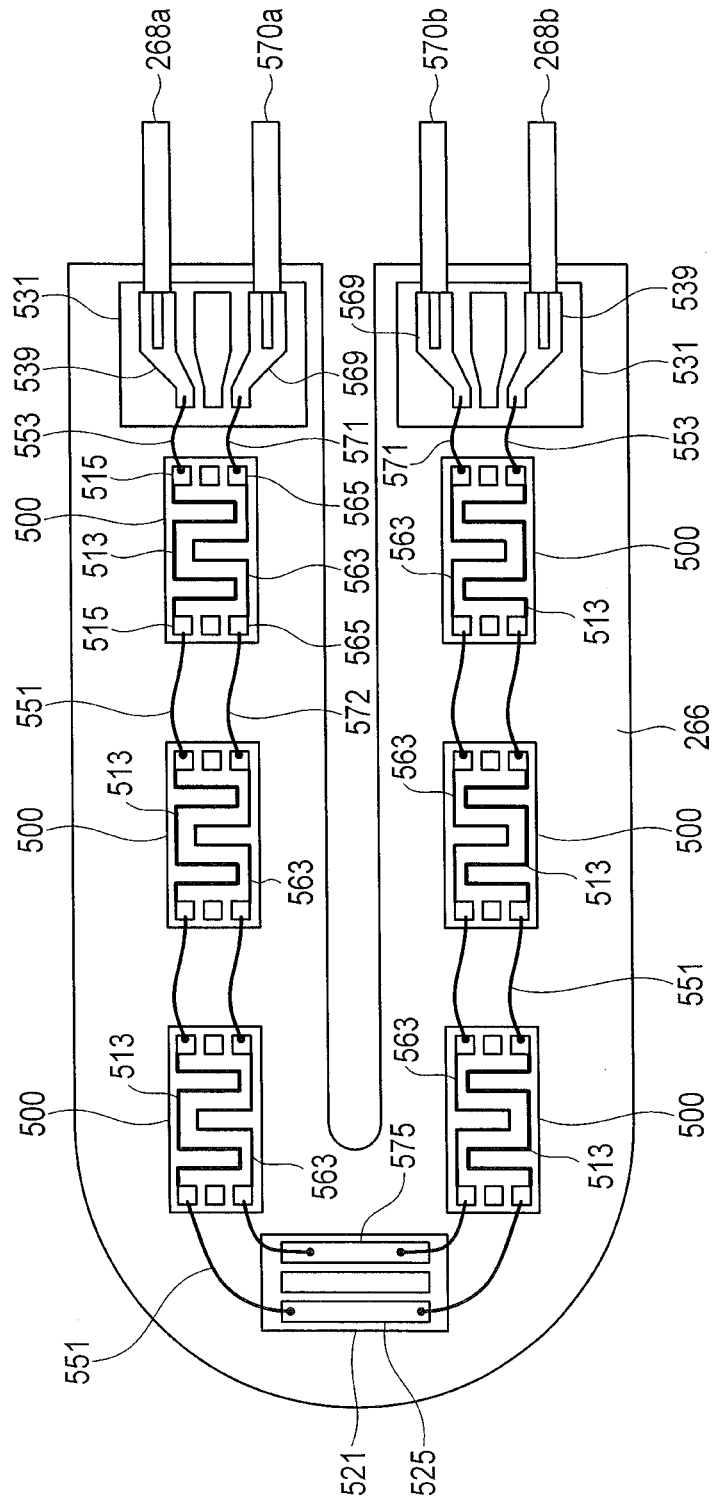
F I G. 12

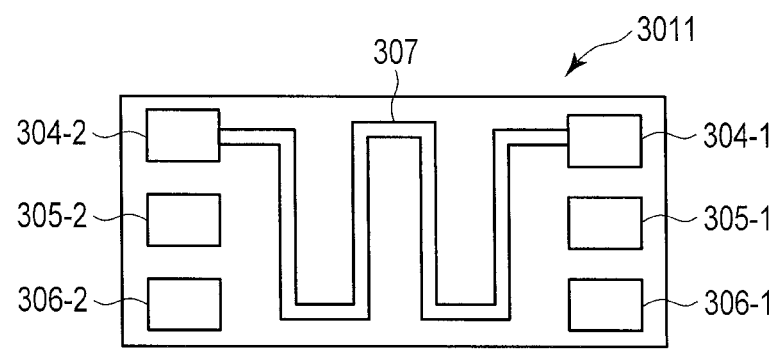
F I G. 14A
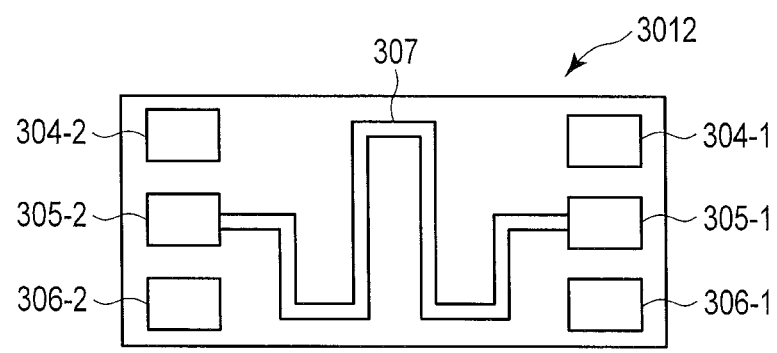
F I G. 14B

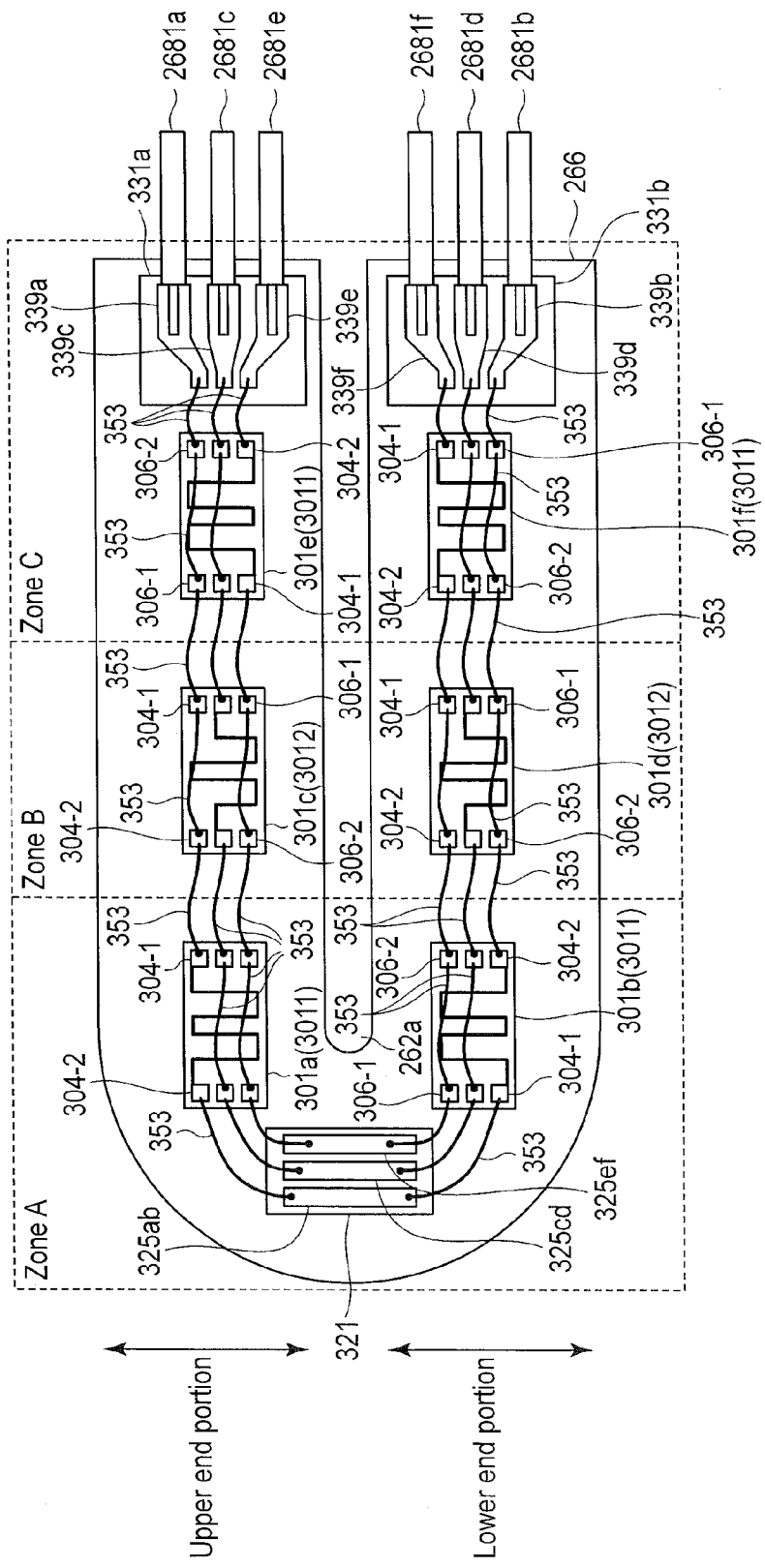
F I G. 15

MEDICAL TREATMENT APPARATUS AND METHOD OF CONTROLLING THE SAME

CROSS REFERENCE TO RELATED APPLICATIONS

This application is a Continuation application of PCT Application No. PCT/JP2011/078542, filed Dec. 9, 2011 and based upon and claiming the benefit of priority from prior Japanese Patent Application No. 2010-278062, filed Dec. 14, 2010, the entire contents of all of which are incorporated herein by reference.

BACKGROUND OF THE INVENTION

1. Field of the Invention

The present invention relates to a medical treatment apparatus and a method of controlling the same.

2. Description of the Related Art

In general, there is known a medical treatment apparatus which treats a living body tissue by using high-frequency energy or thermal energy. For example, Jpn. Pat. Appln. KOKAI Publication No. 2009-247893 discloses the following medical treatment apparatus. That is, this medical treatment apparatus includes an openable holding portion which grips a living body tissue to be treated. A portion of the holding portion which comes into contact with a living body tissue is provided with a high-frequency electrode for applying a high-frequency voltage and a heater member for heating the high-frequency electrode. The holding portion includes a cutter. When using such a medical treatment apparatus, the operator first grips a living body tissue with the holding portion and applies a high-frequency voltage to it. The operator anastomoses the living body tissue with the holding portion by heating the living body tissue with the holding portion. In addition, it is possible to excise the living body tissue with the cutter of the holding portion while a living body tissue end portion is joined.

BRIEF SUMMARY OF THE INVENTION

A medical treatment apparatus like that disclosed in Jpn. Pat. Appln. KOKAI Publication No. 2009-247893 described above is generally manufactured by separately forming a heat transfer portion like the above electrode, of the above holding portion, which comes into contact with a living body tissue and a heater member which heats the heat transfer portion and then joining them together. In this case, in consideration of the ease of wiring, a surface, of the substrate of the heater member, on which a heating member as a heat source is formed generally differs from a surface which is joined to the heat transfer portion. In such a case, since the substrate is located between the heat transfer portion and the heating member, a temperature difference occurs between the heat transfer portion and the heating member. In order to accurately control the heating temperature of a living body tissue, it is necessary to perform control in consideration of the temperature difference between the transfer portion and the heating member.

It is therefore an object of the present invention to provide a medical treatment apparatus which can accurately perform temperature control concerning the heating of a living body tissue in consideration of the temperature difference between the heat transfer portion and the heating member, and a method of controlling the apparatus.

To achieve the above described object, according to an aspect of the invention, a medical treatment apparatus for treating a living body tissue by heating the living body tissue to a target temperature includes a heat transfer portion configured to come into contact with the living body tissue and transfer heat to the living body tissue; a heating chip including a heating region on one surface, joined to the heat transfer portion on the other surface, and configured to heat the heat transfer portion by inputting energy to the heating region; a temperature measurement unit configured to acquire a temperature of the heating region; and a control unit configured to control a temperature of the heat transfer portion to the target temperature by controlling the temperature of the heating region to a temperature differing from the target temperature by an offset value which changes in accordance with an amount of energy input to the heating region, based on the temperature of the heating region which is acquired by the temperature measurement unit.

To achieve the above described object, according to an aspect of the invention, a method of controlling a medical treatment apparatus which includes a heat transfer portion configured to come into contact with a living body tissue and a heating electric resistance pattern configured to heat the heat transfer portion, and is configured to treat the living body tissue by heating the living body tissue to a target temperature by using the heat transfer portion, the method includes acquiring a resistance value of the heating electric resistance pattern; calculating a temperature of the heating electric resistance pattern based on the resistance value of the heating electric resistance pattern; acquiring a current input electric energy for the heating electric resistance pattern; estimating a temperature of the heat transfer portion based on the temperature of the heating electric resistance pattern and the input electric energy; and deciding an electric energy to be input to the heating electric resistance pattern next based on a difference between the estimated temperature of the heat transfer portion and the target temperature.

The present invention can provide a medical treatment apparatus which can control the transfer portion to a target temperature by making the temperature of the heating member differ from the target temperature of the heat transfer portion by an offset value which changes in accordance with the amount of energy input to the heating member, and hence can accurately perform temperature control concerning the heating of a living body tissue, and a method of controlling the apparatus.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic sectional view showing an example of the arrangement of the shaft and holding portion of an energy treatment tool according to the first embodiment, with a holding portion being closed;

FIG. 3A is a plan view schematically showing an example of the arrangement of the first holding member of the holding portion according to the first embodiment;

FIG. 3B is a schematic view showing an example of the arrangement of the first holding member of the holding portion according to the first embodiment, and is a longitudinal sectional view taken along line 3B-3B in FIG. 3A;

FIG. 4A is a plan view schematically showing an example of the arrangement of a heater member according to the first embodiment;

FIG. 4B is a view schematically showing an example of the arrangement of the heater member according to the first embodiment, and is a sectional view taken along line 4B-4B in FIG. 4A;

FIG. 12 is a view schematically showing an example of an arrangement including a first high-frequency electrode, heater members, a relay chip, connection chips, and wires which connect them according to the second embodiment;

FIG. 14A is a schematic view showing an example of the arrangement of a heater member concerning one layout of a medical treatment system according to the third embodiment of the present invention;

FIG. 14B is a schematic view showing an example of the arrangement of a heater member concerning another layout of the medical treatment system according to the third embodiment of the present invention; and FIG. 15 is a view schematically showing an example of an arrangement including a first high-frequency electrode, heater members, a relay chip, connection chips, and wires which connect them according to the third embodiment.

DETAILED DESCRIPTION OF THE INVENTION

[First Embodiment]

Figure 1:
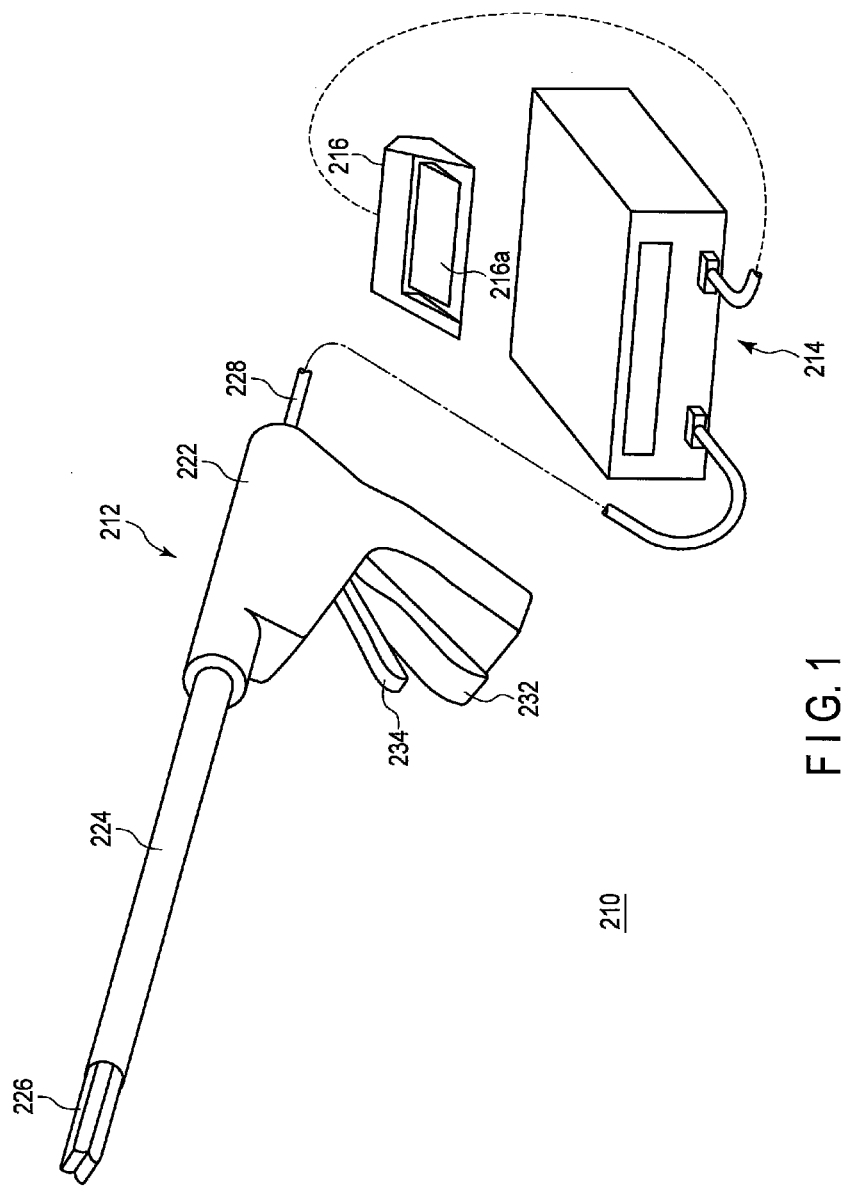
FIG. 1 is a schematic view showing an example of the arrangement of a medical treatment system according to the first embodiment of the present invention.

The first embodiment of the present invention will be described first with reference to the accompanying drawings. A medical treatment apparatus according to this embodiment is an apparatus which applies high-frequency energy and thermal energy to a living body tissue to treat the living body tissue. As shown in FIG. 1, a medical treatment apparatus 210 includes an energy treatment tool 212, an energy source 214, and a foot switch 216.

The energy treatment tool 212 is a linear-type surgical treatment tool for performing treatment upon penetrating through the abdominal wall. The energy treatment tool 212 includes a handle 222, a shaft 224, and a holding portion 226. The holding portion 226 is openable and serves as a treatment portion which performs treatment such as coagulation or incision while holding a living body tissue to be treated. The holding portion 226 is disposed on one end of the shaft 224. The other end of the shaft 224 is connected to the handle 222. For the sake of descriptive convenience, the holding portion 226 side and the handle 222 side will be referred to as the distal end side and the proximal end side, respectively. The handle 222 has a shape that allows the operator to easily grip, for example, an almost L shape. The handle 222 is connected to the energy source 214 via a cable 228. Obviously, the shape of the energy treatment tool 212 shown here is an example, and may have another shape as long as it has the same function. For example, the energy treatment tool 212 may have a forceps-like shape or have a curved shaft.

The foot switch 216 having a pedal 216a is connected to the energy source 214. The foot switch 216 which is operated by a foot of the operator may be replaced with a switch which is operated by a hand of the operator or another type of switch. The operator operates the pedal 216a of the foot switch 216 to ON/OFF-switch the energy source 214 to or not to supply energy to the energy treatment tool 212.

The handle 222 includes a holding portion opening/closing knob 232 and a cutter driving knob 234. The holding portion opening/closing knob 232 is coupled to the proximal end of a sheath 244 of the shaft 224 (to be described later). As the holding portion opening/closing knob 232 moves close and away from the handle 222, the sheath 244 moves along the axial direction of the shaft 224. As a consequence, the holding portion 226 opens and closes. The cutter driving knob 234 is a knob which is juxtaposed to the holding portion opening/closing knob 232 and moves a cutter 254 (to be described later).

Figure 2B:
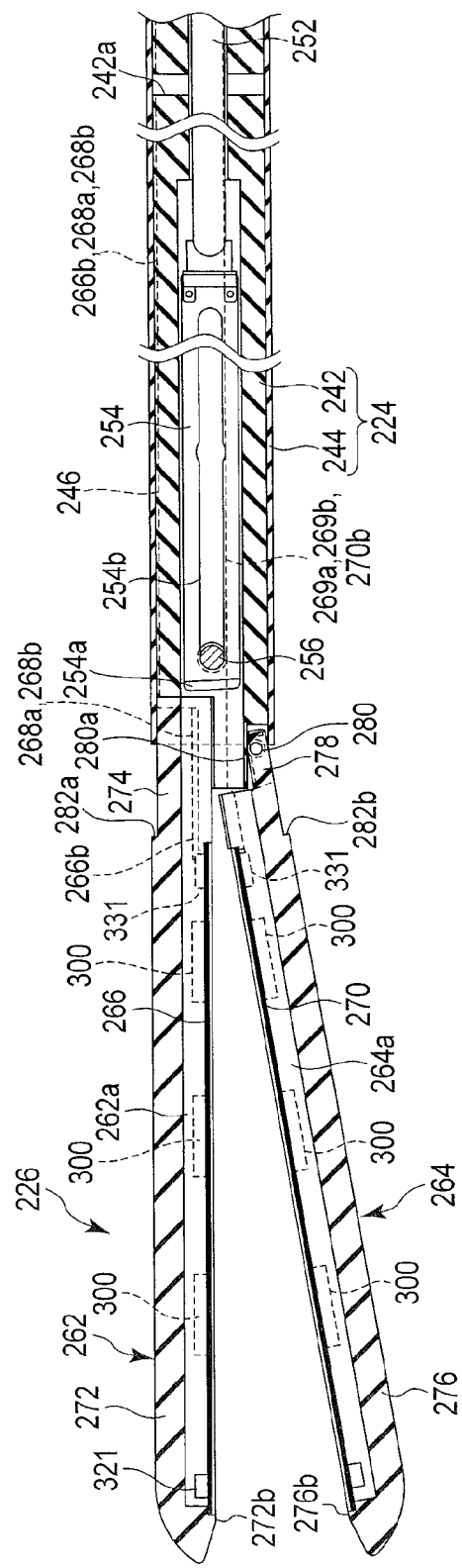
FIG. 2B is a schematic sectional view showing an example of the arrangement of the shaft and holding portion of the energy treatment tool according to the first embodiment, with the holding portion being open.

FIGS. 2A and 2B each show an example of the structure of the holding portion 226 and shaft 224. FIG. 2A shows a state in which the holding portion 226 is closed. FIG. 2B shows a state in which the holding portion 226 is open. The shaft 224 includes a cylindrical body 242 and the sheath 244. The cylindrical body 242 is fixed to the handle 222 at the proximal end portion. As shown in FIGS. 2A and 2B, the sheath 244 is disposed on the outer circumference of the cylindrical body 242 so as to be slidable along the axial direction of the cylindrical body 242. The holding portion 226 is disposed on the distal end portion of the cylindrical body 242.

The holding portion 226 includes a first holding member 262 and a second holding member 264. The first and second holding members 262 and 264 each preferably have an insulation property as a whole. The first holding member 262 includes a first holding member main body 272 and a base portion 274 provided on the proximal end side of the first holding member main body 272. Likewise, the second holding member 264 integrally includes a second holding member main body 276 and a base portion 278 provided on the proximal end side of the second holding member main body 276. The base portion 274 of the first holding member 262 is fixed to the distal end portion of the cylindrical body 242 of the shaft 224. On the other hand, the base portion 278 of the second holding member 264 is pivotally supported on the distal end portion of the cylindrical body 242 of the shaft 224 by a support pin 280 disposed in a direction perpendicular to the axial direction of the shaft 224. The second holding member 264 pivots about the axis of the support pin 280 to open and close the first holding member 262.

The outer surface shapes of the first and second holding members 262 and 264 are smooth curved surfaces. While the second holding member 264 is closed relative to the first holding member 262, a sectional shape of the first and second holding member main bodies 272 and 276 in a joined state is almost circular or elliptic. In the closed state, a sectional shape of the base portion 274 of the first holding member 262 and the base portion 278 of the second holding member 264 is almost circular or elliptic. In this case, the diameter of the first and second holding member main bodies 272 and 276 is larger than that of the base portion 274 of the first holding member 262 and the base portion 278 of the second holding member 264. A stepped portion 282a is formed between the first holding member main body 272 and the base portion 274 of the first holding member 262. A stepped portion 282b is formed between the second holding member main body 276 and the base portion 278 of the second holding member 264.

An elastic member 280a, for example, a leaf spring, biases the second holding member 264 to open it relative to the first holding member 262. Sliding the sheath 244 to the distal end side relative to the cylindrical body 242 to cover the base portion 274 of the first holding member 262 and the base portion 278 of the second holding member 264 will close the first holding member 262 and the second holding member 264 against the biasing force of the elastic member 280a, as shown in FIG. 2A. On the other hand, sliding the sheath 244 to the proximal end of the cylindrical body 242 will open the second holding member 264 relative to the first holding member 262 owing to the biasing force of the elastic member 280a, as shown in FIG. 2B.

As shown in FIGS. 2A and 2B, a recess portion 246 is formed in the cylindrical body 242 along the axial direction of the cylindrical body 242. A first high-frequency electrode conducting line 266b connected to a first high-frequency electrode 266 (to be described later) and heater member conducting lines 268a and 268b connected to a heater member 300 as a heating member are disposed in the recess portion 246. A second high-frequency electrode conducting line 270b connected to a second high-frequency electrode 270 (to be described later) and heater member conducting lines 269a and 269b connected to the heater member 300 as a heating member extend through the cylindrical body 242.

A driving rod 252 is disposed in the cylindrical body 242 so as to be movable along the axial direction of the cylindrical body 242. The thin plate-like cutter 254 is disposed on the distal end side of the driving rod 252. The distal end side of the cutter 254 is a free end, on which a blade 254a is formed. The proximal end side of the cutter 254 is fixed to the driving rod 252. A long slit 254b is formed between the distal end side and proximal end side of the cutter 254. A movement regulation pin 256 extending in a direction perpendicular to the axial direction of the shaft 224 and the planar direction of the cutter 254 and fixed to the cylindrical body 242 extends through the long slit 254b. The proximal end side of the driving rod 252 to which the cutter 254 is fixed is connected to the cutter driving knob 234. Operating the cutter driving knob 234 will move the cutter 254 along the axial direction of the cylindrical body 242 through the driving rod 252. In this case, the cutter 254 moves while being regulated by the movement regulation pin 256 and the long slit 254b. Note that lock portions 254c for locking the movement regulation pin 256 and controlling the movement of the cutter 254 are formed at at least three positions at one end and the other end of the long slit 254b of the cutter 254 and between one end and the other end. When moving to the distal end side, the cutter 254 is fitted in a cutter guide groove 262a formed in the first holding member 262 (to be described later) and a cutter guide groove 264a formed in the second holding member 264.

In order to discharge water vapor, tissue fluid, and the like (to be described later), fluid discharge ports 242a and 244a are respectively formed on the proximal end sides of the cylindrical body 242 and sheath 244 such that the positions of the ports coincide with each other while the holding portion 226 is closed (the state in FIG. 2A). Although not shown here, the outer circumferential surface of the fluid discharge port 244a of the sheath 244 is preferably provided with a connection mouthpiece. Performing suction through the connection mouth piece causes fluids such as water vapor and a liquid discharged from a living body tissue to be discharged through the cutter guide grooves 262a and 264a, the interior of the cylindrical body 242, the fluid discharge port 242a of the cylindrical body 242, the fluid discharge port 244a of the sheath 244, and the connection mouthpiece. Although the fluid discharge ports 242a and 244a are preferably provided in the shaft 224, they may be provided in the handle 222.

Figure 3C:
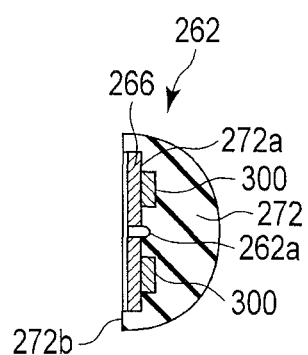
FIG. 3C is a schematic view showing an example of the arrangement of the first holding member of the holding portion according to the first embodiment, and is a cross-sectional view taken along line 3C-3C in FIG. 3A.

As shown in FIGS. 3A, 3B, and 3C, the cutter guide groove 262a for guiding the cutter 254 described above is formed in the first holding member main body 272 and the base portion 274. A recess portion 272a and a holding surface 272b including the edge portion of the recess portion 272a are formed on the first holding member main body 272. The first high-frequency electrode 266 formed from, for example, a thin copper plate is disposed in the recess portion 272a. Since the first high-frequency electrode 266 has the cutter guide groove 262a, its planar shape is almost U-shaped, as shown in FIG. 3A. The surface of the first high-frequency electrode 266 comes into contact with the living body tissue.

When the holding portion 226 is closed, the holding surface 272b comes into contact with a holding surface 276b of the second holding member 264 facing the holding surface 272b (to be described later). When the holding portion 226 is closed, the first high-frequency electrode 266 does not come into contact with the second high-frequency electrode 270 facing the first high-frequency electrode 266 (to be described later). While the holding portion 226 is closed, there is a gap between the first high-frequency electrode 266 and the second high-frequency electrode 270. However, since the living body tissue easily deforms, when the holding portion 226 in a closed state grips the living body tissue, the gripped living body tissue deforms in conformity with the gap and comes into contact with the first high-frequency electrode 266 and the second high-frequency electrode 270.

As shown in FIGS. 2A and 2B, the first high-frequency electrode 266 is electrically connected to the first high-frequency electrode conducting line 266b. The first high-frequency electrode 266 is connected to the cable 228 via the first high-frequency electrode conducting line 266b.

The cutter guide groove 264a is formed in the second holding member 264 at a position facing the cutter guide groove 262a. The cutter guide groove 262a of the first holding member 262 and the cutter guide groove 264a of the second holding member 264 can guide the cutter 254. The second holding member main body 276 is provided with the second high-frequency electrode 270 symmetrical in shape with the first high-frequency electrode 266 at a position facing the first high-frequency electrode 266. The second high-frequency electrode 270 is connected to the cable 228 via the second high-frequency electrode conducting line 270b.

The first and second holding member main bodies 272 and 276 each further have a mechanism for generating heat for cauterization of the living body tissue in contact with the first and second high-frequency electrodes 266 and 270. The heating mechanism provided on the first holding member main body 272 has the same configuration as that provided on the second holding member main body 276. The heating mechanism provided on the first holding member main body 272 will therefore be exemplified below. The heater member 300, a relay chip 321, and a connection chip 331 composing this heating mechanism will be described first.

The heater member 300 will be described with reference to FIGS. 4A and 4B. The heater member 300 is a heating member which generates heat. The heater member 300 is formed by using an alumina substrate 311. A resistance pattern 313 as a Pt thin film for heat generation is formed on the upper surface of the substrate 311, which is one of the principal surfaces. A pair of rectangular electrodes 315 respectively connected to the two ends of the resistance pattern 313 are formed on the upper surface of the substrate 311. A polyimide film 317 for insulation is formed on the upper surface of the substrate 311 including the surface of the resistance pattern 313, except for the portion on which electrodes 315 are formed. A joining metal layer 319 is formed on the entire lower surface of the substrate 311. Electrodes 315 and the metal layer 319 are multilayer films formed from, for example, Ti, Cu, Ni, and Au. Electrodes 315 and the metal layer 319 have stable strength with respect to wire bonding and soldering. The joining metal layer 319 is provided to stabilize joining when soldering the heater member 300 to the first high-frequency electrode 266.

Figure 5A:
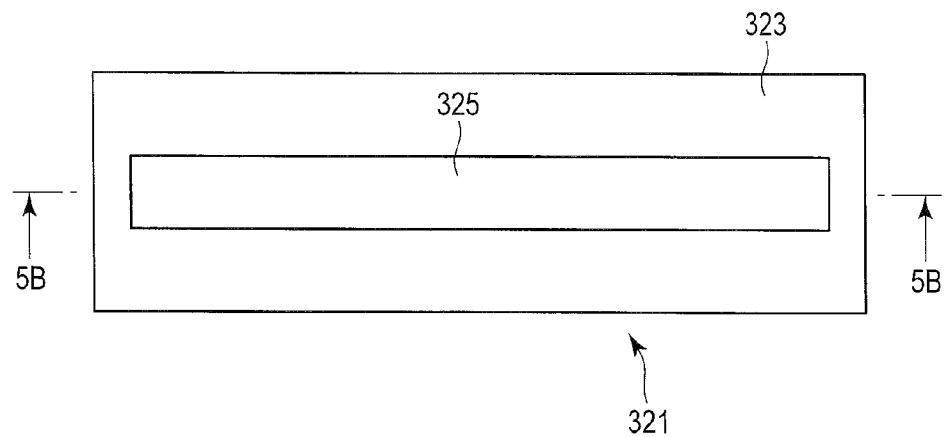
FIG. 5A is a plan view schematically showing an example of the arrangement of a relay chip according to the first embodiment.
Figure 5B:
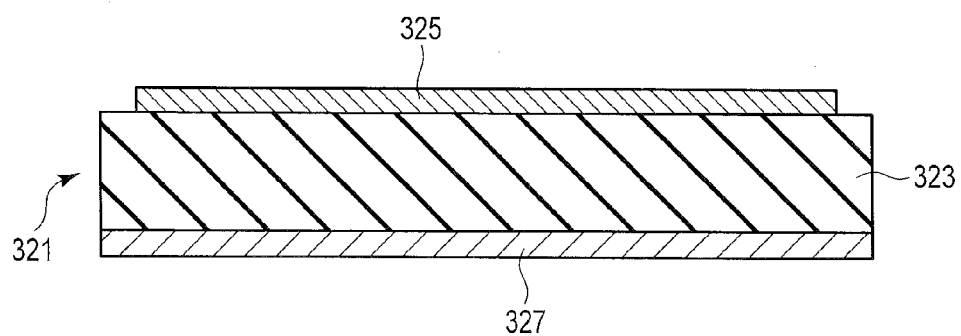
FIG. 5B is a view schematically showing an example of the arrangement of the relay chip according to the first embodiment, and is a sectional view taken along line 5B-5B in FIG. 5A.
Figure 6:
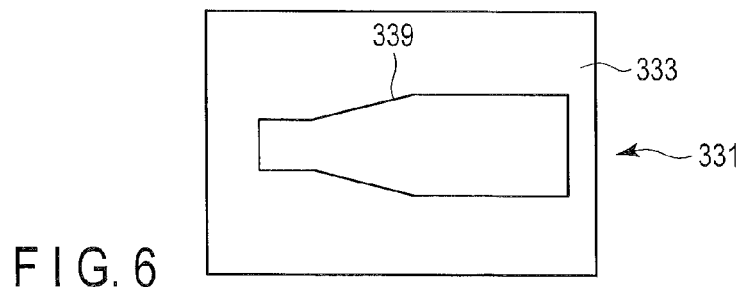
FIG. 6 is a plan view schematically showing an example of the arrangement of a connection chip according to the first embodiment.

The relay chip 321 will be described next with reference to FIGS. 5A and 5B. Like the heater member 300, the relay chip 321 is formed by using an alumina substrate 323. A rectangular electrode 325 is formed on the upper surface of the substrate 323. A joining metal layer 327 is formed on the entire lower surface of the substrate 323. The connection chip 331 has the same configuration as that of the relay chip 321. As shown in FIG. 6, the connection chip 331 includes an alumina substrate 333, an electrode 339 formed on the upper surface of the substrate 333, and a joining metal layer formed on the entire lower surface of the substrate 333.

The heater member 300, the relay chip 321, and the connection chip 331 are disposed on the surface (lower surface) of the first high-frequency electrode 266 on the opposite side to the surface which comes into contact with a living body tissue. In this case, the heater member 300, the relay chip 321, and the connection chip 331 are fixed by soldering the upper surface of the joining metal layer to the lower surface of the first high-frequency electrode 266. The first high-frequency electrode 266, the resistance pattern 313, electrode 325, and electrode 339 are insulated by the substrates 311, 323, and 333 in this manner.

Figure 7:
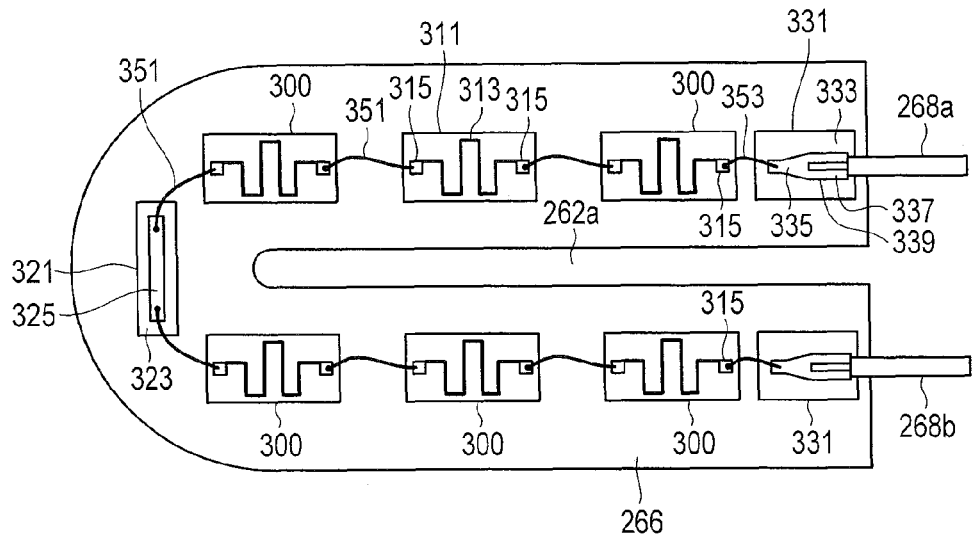
FIG. 7 is a view showing an example of an arrangement including a first high-frequency electrode, heater members, a relay chip, and connection chips, and wires which connect them according to the first embodiment.

The six heater members 300 are joined to the first high-frequency electrode 266, as shown in FIG. 7. That is, the heater members 300 are arranged three by three in two rows on the two sides of the cutter guide groove 262a in the longitudinal direction of the first high-frequency electrode 266. The relay chip 321 is disposed on the distal end portion of the first high-frequency electrode 266. In addition, the connection chips 331 each are arranged at symmetrical positions with respect to the cutter guide groove 262a on the proximal end portion of the first high-frequency electrode 266.

Heater member conducting line 268a is soldered to a base portion 337 of the connection chip 331. Heater member conducting line 268b is soldered to the base portion 337 of the other connection chip 331. Heater member conducting line 268a and heater member conducting line 268b are paired and connected to the energy source 214 via the cable 228. A distal end portion 335 of the connection chip 331 and electrodes 315 of the heater member 300 nearest to the distal end portion 335 are connected to each other via a wire 353 formed by wire bonding. Electrodes 315 of the heater members 300 adjacent to each other in the longitudinal direction are connected to each other through wires 351 formed by wire bonding.

At the distal end portion of the first high-frequency electrode 266, electrodes 315 of the heater members 300 are connected via electrode 325 of the relay chip 321 by using the wires 351 formed by wire bonding. That is, one electrode 315 of the heater member 300 located at the most distal end is connected to electrode 325 of the relay chip 321 via the wire 351. The other electrode 315 of the heater member 300 located at the most distal end is also connected to electrode 325 of the relay chip 321 via the wire 351. The reason why they are connected to each other via the relay chip 321 is that the interval between the two heater members 300 arranged in a direction perpendicular to the longitudinal direction of the first high-frequency electrode 266 at the distal end portion of first high-frequency electrode 266 is larger than the interval between the heater members 300 arranged side by side in the longitudinal direction of the first high-frequency electrode 266, and it is difficult to connect them by wire bonding.

In this manner, the six heater members 300, the relay chip 321, and the connection chips 331 arranged in a U shape are connected in series via the wires 351. The current output from the energy source 214 reaches the connection chip 331 via heater member conducting line 268a and flows in the resistance pattern 313 of the heater member 300 via the wire 351. As a result, the resistance pattern 313 generates heat. When each resistance pattern 313 generates heat, the heat conducts to the first high-frequency electrode 266. As a result, the living body tissue in contact with the first high-frequency electrode 266 is cauterized. Note that the first holding member main body 272 preferably covers the outer circumference of the heater member 300 and has a thermal insulation property. This structure implements thermal conduction with little loss.

When manufacturing the medical treatment apparatus of this embodiment, it is possible to use a die bonder used for the manufacturing of general semiconductor devices for soldering to fix ceramic chips such as the heater members 300, the relay chip 321, and the connection chips 331 to the first high-frequency electrode 266. In addition, since the heater members 300 and the relay chip 321 are discretely arranged in a U shape in conformity with the shape of the first high-frequency electrode 266 and the adjacent chips are connected in series, the distance between the adjacent chips is relatively short, for example, about 5 mm. Since the connection distance is relatively short, it is possible to connect the adjacent chips to each other by wire bonding. For this wire bonding, a wire bonder used for the manufacture of general semiconductor devices. The manufacture using a die bonder or wire bonder exhibits very high productivity and can be performed at a low cost.

Note that in this embodiment, the heater member 300 has, for example, a length of about 3 mm and a width of about 1.2 mm. In addition, the first high-frequency electrode 266 has, for example, a length of about 35 mm in the longitudinal direction and a width of about 7 mm. The cutter guide groove 262a having a width of about 1 mm is cut in the first high-frequency electrode 266 along its central axis.

Figure 8:
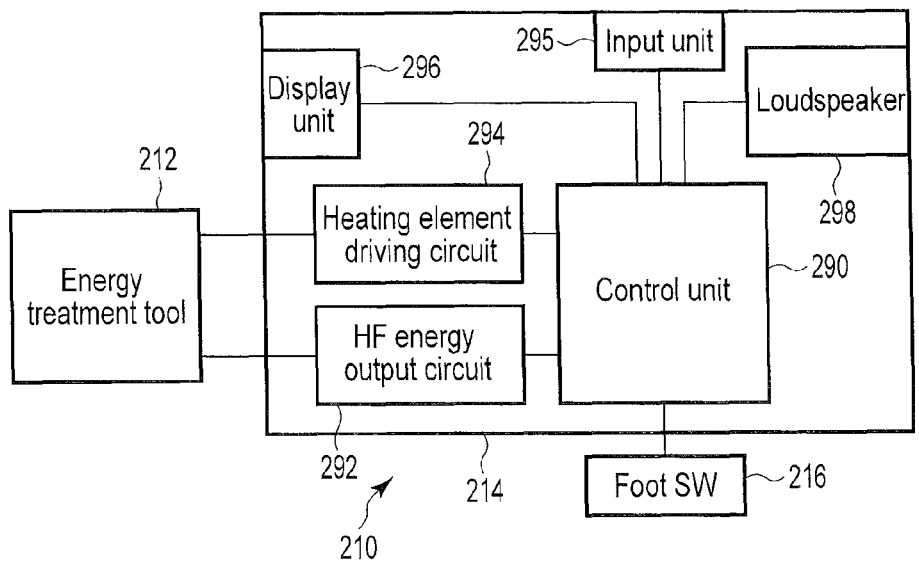
FIG. 8 is a view showing an example of the arrangement of an energy source according to the first embodiment.

As shown in FIG. 8, a control unit 290, a high-frequency (HF) energy output circuit 292, a heating element driving circuit 294, an input unit 295, a display unit 296, and a loudspeaker 298 are arranged in the energy source 214. The high-frequency energy output circuit 292, the heating element driving circuit 294, the input unit 295, the display unit 296, and the loudspeaker 298 are connected to the control unit 290. The control unit 290 controls the respective units of the energy source 214. The high-frequency energy output circuit 292 is connected to the energy treatment tool 212, and drives the first and second high-frequency electrodes 266 and 270 of the energy treatment tool 212 under the control of the control unit 290. The heating element driving circuit 294 is connected to the energy treatment tool 212, and drives the heater members 300 of the energy treatment tool 212 under the control of the control unit 290. The foot switch (SW) 216 is connected to the control unit 290. The foot switch 216 inputs an ON signal and an OFF signal into the control unit 290, the ON signal indicating the energy treatment tool 212 performs treatment and the OFF signal indicating the energy treatment tool 212 stops treatment. The input unit 295 inputs various types of settings to the control unit 290. The display unit 296 displays various types of settings for the control unit 290. The loudspeaker 298 outputs an alarm sound and the like.

Note that the high-frequency energy output circuit 292 can output high-frequency energy and detects an impedance Z. That is, the high-frequency energy output circuit 292 has a sensor function of measuring the impedance Z of the living body tissue between the first and second high-frequency electrodes 266 and 270 of the energy treatment tool 212. The heating element driving circuit 294 supplies energy to the heater members 300 to cause them to generate heat, and has a sensor function of measuring a heating temperature T of the heater members 300.

The operation of the medical treatment apparatus 210 according to this embodiment will be described next. The operator operates the input unit 295 of the energy source 214 in advance to set output conditions for the medical treatment apparatus 210. More specifically, the operator sets a set power Pset [W] for a high-frequency energy output, a set temperature Tset [° C.] for a thermal energy output, a heating time t [s], and the like in advance. This apparatus may be configured to individually set the respective values or select a set of set values in accordance with an operative method.

The operator inserts the holding portion 226 and shaft 224 of the energy treatment tool 212 into the abdominal cavity through, for example, the abdominal wall while the holding portion 226 is closed as shown in FIG. 2A. When the holding portion 226 approaches the living body tissue to be treated, the operator operates the holding portion opening/closing knob 232 of the handle 222 to open/close the first and second holding members 262 and 264 to grip the living body tissue to be treated. That is, first of all, the operator moves the sheath 244 to the proximal end side relative to the cylindrical body 242. As a consequence, the second holding member 264 opens relative to the first holding member 262 owing to the biasing force of the elastic member 280a.

While the holding portion 226 is open, the living body tissue is placed between the first holding member 262 and the second holding member 264. In this state, the operator moves the sheath 244 to the distal end side relative to the cylindrical body 242. As a consequence, the 244 closes the second holding member 264 relative to the first holding member 262 against the biasing force of the elastic member 280a. In this manner, the holding portion 226 grips the living body tissue to be treated together with the first and second holding members 262 and 264. At this time, the living body tissue to be treated is in contact with both the first high-frequency electrode 266 provided for the first holding member 262 and the second high-frequency electrode 270 provided for the second holding member 264.

When gripping the living body tissue to be treated with the holding portion 226, the operator operates the foot switch 216. When the operator switches the foot switch 216 to ON, the energy source 214 supplies high-frequency power with the set power Pset [W] set in advance to the first and second high-frequency electrodes 266 and 270 via the cable 228. The supplied power is, for example, about 20 to 80 W. In this manner, a high-frequency current flows in the living body tissue to be treated which is gripped between the first holding member 262 and the second holding member 264. As a result, the living body tissue is heated and cauterized (denatured).

At the time of tissue cauterization, fluids (for example, a liquid such as blood and/or water vapor) are discharged from the living body tissue. At this time, the holding surface 272b of the first holding member 262 and the holding surface 276b of the second holding member 264 protrude from the first and second high-frequency electrodes 266 and 270. For this reason, holding surface 272b and holding surface 276b function as barrage portions (dams) to keep the fluids inside the first and second holding members 262 and 264.

Performing suction through the fluid discharge port 244a of the sheath 244 and the fluid discharge port 242a of the cylindrical body 242 will make the fluids staying in the first and second holding members 262 and 264 flow in the cutter guide grooves 262a and 264a and the cylindrical body 242. The fluids are then discharged from the fluid discharge port 242a and the fluid discharge port 244a. While fluids are discharged from the living body tissue, the fluids are kept discharged in the above manner. This prevents the occurrence of thermal spreading due to fluids discharged from the living body tissue with raised temperature, and hence can prevent the fluids from affecting portions which are not to be treated.

The energy source 214 then supplies power to each heater member 300 to raise its temperature to the temperature Tset [° C.] set in advance. In this case, the set temperature Tset is, for example, 100 to 300° C. At this time, a current flows from the energy source 214 into the resistance pattern 313 of each heater member 300 disposed on the first high-frequency electrode 266 via the cable 228, heater member conducting line 268a, the connection chip 331, and the wire 353 formed by wire bonding. This current causes the resistance pattern 313 to generate heat. The heat generated by the resistance pattern 313 conducts to the first high-frequency electrode 266 via the substrate 311 and the metal layer 319. As a result, the temperature of the first high-frequency electrode 266 rises. Likewise, a current flows to the resistance pattern 313 of each heater member 300 disposed on the second high-frequency electrode 270 via the cable 228 and the 269a. At this time, the resistance pattern 313 generates heat. This heat conducts to the second high-frequency electrode 270. The temperature of the second high-frequency electrode 270 therefore rises. As a result, the living body tissue in contact with the first and second high-frequency electrodes 266 and 270 is coagulated.

When the living body tissue is coagulated, the operator stops outputting high-frequency energy and thermal energy. Finally, the operator operates the cutter driving knob 234. As a consequence, the cutter 254 moves in the cutter guide grooves 262a and 264a and cuts the living body tissue. With the above operation, the operator completes treatment on the living body tissue.

If the resistance pattern 313 is formed on the joint surface between the first high-frequency electrode 266 and the heater member 300, it is difficult to perform wiring. In this embodiment, therefore, the resistance pattern 313 is formed on a principal surface of the heater member 300 which differs from the joint surface (on which the metal layer 319 is formed) with the first high-frequency electrode 266. As described above, in consideration of wiring, the resistance pattern 313 is generally formed on a surface of the heater member 300 which differs from the joint surface with the first high-frequency electrode 266.

However, since the substrate 311 exists between the resistance pattern 313 and the first high-frequency electrode 266 whose temperature should be accurately controlled because it comes into contact with the living body tissue to be treated, a temperature difference occurs between the first high-frequency electrode 266 and the resistance pattern 313. This temperature difference changes in accordance with the states of the first high-frequency electrode 266, resistance patterns 313, and living body tissue. As in this embodiment, in particular, when the small heater members 300 heat the large first high-frequency electrode 266, the heat flux density from each resistance pattern 313 to the first high-frequency electrode 266 is high. In this case, a large temperature difference occurs. The embodiment is configured to control an input to each resistance pattern 313 in consideration of this temperature difference to keep the temperature of the first high-frequency electrode 266 at the set temperature Tset.

A method of controlling the temperature of the first high-frequency electrode 266 constantly at the set temperature Tset in this embodiment will be described. The embodiment is configured to acquire the temperature of each resistance pattern 313, based on the resistance of the resistance pattern 313 of the heater member 300, and control the temperature of the first high-frequency electrode 266 constantly at the set temperature Tset in consideration of the temperature difference between the resistance pattern 313 and the first high-frequency electrode 266.

Figure 9:
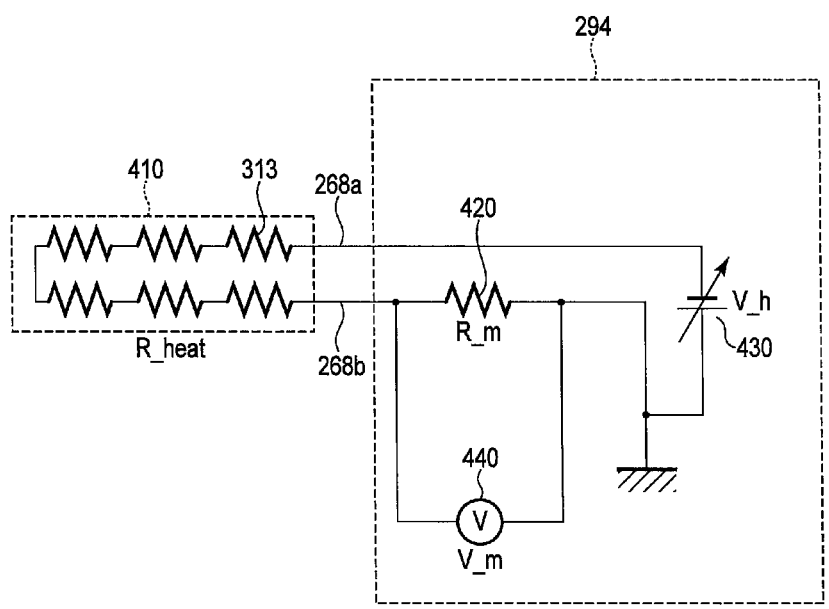
FIG. 9 is a view showing an example of the circuit configuration of the medical treatment system according to the first embodiment.

A circuit concerning the acquisition of the temperature of each resistance pattern 313 will be described with reference to FIG. 9. Referring to FIG. 9, a heater resistor 410 indicates the total resistance of six resistance patterns 313 connected in series. In this case, the resistance of the heater resistor 410 is represented by R_heat. The heater resistor 410 is connected in series with a monitor resistor 420. The resistance of the monitor resistor 420 is represented by R_m. A variable voltage source 430 is connected to the heater resistor 410 and the monitor resistor 420. In this case, the voltage applied by the variable voltage source 430 is represented by V_h. A voltage measuring device 440 is connected between the two terminals of the monitor resistor 420 to measure the potential difference between them. In this case, the potential difference measured by the voltage measuring device 440 is represented by V_m. Assume that in this embodiment, the voltage V_h applied by the variable voltage source 430 changes at any time in accordance with the potential difference V_m of the monitor resistor 420. Note that the monitor resistor 420, the variable voltage source 430, and the voltage measuring device 440 are arranged in the heating element driving circuit 294. In addition, the control unit 290 controls the variable voltage source 430 and the voltage measuring device 440.

As described above, for example, the holding portion 226 functions as a holding member which grips a living body tissue. For example, the first or second high-frequency electrode 266 or 270 functions as a heat transfer portion configured to come into contact with the living body tissue and transfer heat to the living body tissue. For example, the heater member 300 functions as a heating chip which heats the heat transfer portions. For example, the resistance pattern 313 functions as a heating region disposed on one surface of the heating chip. For example, the voltage measuring device 440 functions as a temperature measurement unit configured to acquire the temperature of the heating portion. For example, the control unit 290 functions as a control unit configured to control the temperature of the heat transfer portion to a target temperature.

Figure 10:
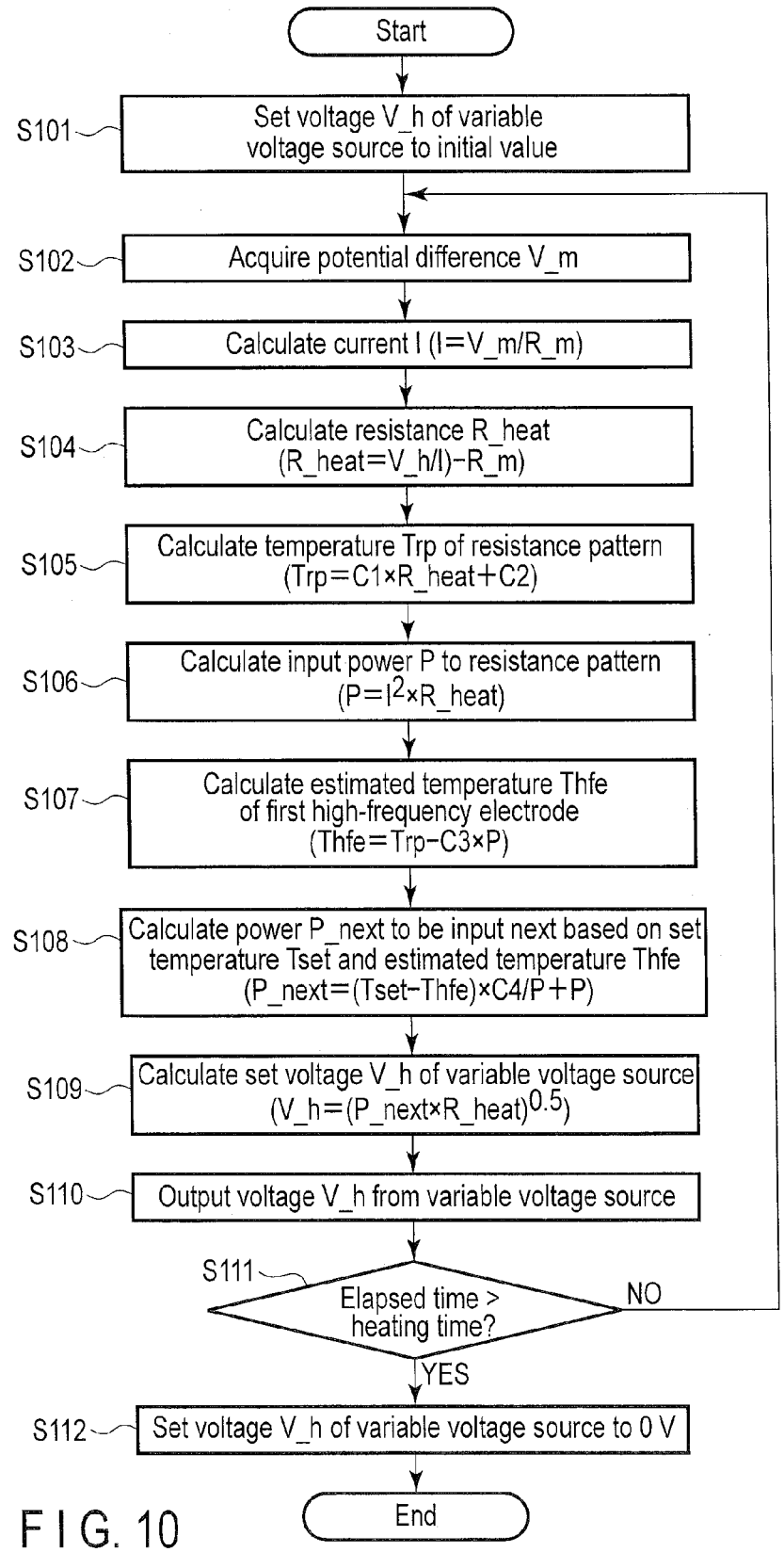
FIG. 10 is a flowchart showing an example of processing by the control unit of the medical treatment system according to the first embodiment.

The processing of controlling the temperature of the first high-frequency electrode 266 at the set temperature Tset by the control unit 290 will be described with reference to the flowchart of FIG. 10.

In step S101, the control unit 290 sets the output voltage V_h of the variable voltage source 430 to an initial value. At the start of control, the temperature of each resistance pattern 313 is unknown. Assuming that the temperature of the resistance pattern 313 is equal to the body temperature, the applied voltage V_h obtained in the following manner is set as an initial value in advance. The variable voltage source 430 applies the set output voltage V_h to the resistance pattern 313.

In step S102, the control unit 290 acquires the potential difference V_m between the two terminals of the monitor resistor 420 which is measured by the voltage measuring device 440.

In step S103, the control unit 290 calculates a current I flowing in the resistance pattern 313 and the monitor resistor 420 based on the acquired potential difference V_m. In this case, since the resistance R_m of the monitor resistor 420 is known, the current I is calculated by $$I = V\_m/R\_m. \tag{1}$$

In step S104, the control unit 290 calculates the resistance R_heat of the heater resistor 410 by using the calculated current I. In this case, the resistance R_heat is calculated by $$R\_heat = (V\_h/I) - R\_m. \tag{2}$$

In step S105, the control unit 290 calculates a temperature Trp of the resistance pattern 313 by using the calculated resistance R_heat. It is known that the relationship between the temperature Trp of the resistance pattern 313 and the resistance R_heat of the heater resistor 410 is represented by equation (3) given below.

$$Trp = C1 \times R\_heat + C2, \tag{3}$$

where C1 and C2 are constants. Constants C1 and C2 are obtained in advance experimentally or in a numerically analytical manner. It is possible to calculate the temperature Trp of the resistance pattern 313 based on equation (3).

In step S106, the control unit 290 calculates an input power P input to the resistance pattern 313. In this case, the input power P is calculated by $$P = I^2 \times R\_\text{heat}. \quad (4)$$

In step S107, the control unit 290 calculates an estimated temperature Thfe of the first high-frequency electrode 266. A temperature difference ΔT between the temperature Trp of the resistance pattern 313 and the temperature of the first high-frequency electrode 266 is almost proportional to a heat flux density q from the resistance pattern 313 to the first high-frequency electrode 266. In this case, the heat flux density q from the resistance pattern 313 to the first high-frequency electrode 266 is almost proportional to the input power P to the resistance pattern 313. The temperature difference ΔT between the temperature Trp of the resistance pattern 313 and the temperature of the first high-frequency electrode 266 can therefore be represented by equation (5) given below using a constant C3.

$$\Delta T = C3 \times P. \quad (5)$$

As described above, the estimated temperature Thfe of the first high-frequency electrode 266 is calculated by equation (6) using the temperature Trp of the resistance pattern 313.

$$\text{Thfe} = \text{Trp} - C3 \times P. \quad (6)$$

Constant C3 may be calculated based on physical property values such as the size and material of the heater member 300. In general, constant C3 is proportional to the thickness of the substrate 311 and inversely proportional to the area and thermal conductivity of the substrate 311. In addition, constant C3 may be obtained by actually measuring the temperatures of the resistance pattern 313 and first high-frequency electrode 266 with respect to various input powers in experiments. Note that the temperature of the first high-frequency electrode 266 can be regarded as equal to that of the joining metal layer 319.

In step S108, the control unit 290 calculates a power P_next to be input next based on the set temperature Tset and the estimated temperature Thfe of the first high-frequency electrode 266. This embodiment is configured to perform simple control operation of changing the current input power P at a rate proportional to the temperature difference between the set temperature Tset and the estimated temperature Thfe of the first high-frequency electrode 266. The power P_next to be input next is represented by $$P\_\text{next} = (T\text{set} - Th\text{fe}) \times C4 / P + P, \quad (7)$$

where C4 is a constant and represents a gain.

In step S109, the control unit 290 calculates the voltage V_h of the variable voltage source to input the power P_next set in step S108. In this case, the voltage V_h of the variable voltage source is calculated by $$V\_h = (P\_\text{next} \times R\_\text{heat})^{0.5}. \quad (8)$$

In step S110, the control unit 290 causes the variable voltage source to output the output voltage V_h set in step S109.

In step S111, the control unit 290 determines whether an elapsed time from the start of control has exceeded the preset heating time t. If this determination result indicates that the elapsed time has not exceeded the heating time, the process returns to step S102 to repeat the same processing as that described above. If the determination result in step S111 indicates that the elapsed time has exceeded the heating time, the process advances to step S112.

In step S112, the control unit 290 sets the voltage V_h of the variable voltage source to 0 V and terminates the processing.

According to the temperature control method of this embodiment, since the temperature of the first high-frequency electrode 266 is estimated by using the input power P to the resistance pattern 313, there is no need to separately dispose a temperature sensor for measuring the temperature of the first high-frequency electrode 266. This makes it possible to obtain a low-cost, compact medical treatment apparatus.

This embodiment also considers the temperature difference between the resistance pattern 313 and the first high-frequency electrode 266. More specifically, the power P_next to be input next, which is decided in step S108, is calculated based on the set temperature Tset and the estimated temperature Thfe of the first high-frequency electrode 266. In step S107, the estimated temperature Thfe is calculated considering that it differs from the temperature Trp of the resistance pattern 313 by the temperature difference ΔT proportional to the input electric energy P. That is, the temperature of the resistance pattern 313 is controlled to a temperature which differs from the set temperature Tset by the temperature difference ΔT (offset value) proportional to the input electric energy P. This makes it possible to accurately control the temperature of the first high-frequency electrode 266.

It is assumed in this embodiment that the temperature difference ΔT between the resistance pattern 313 and the first high-frequency electrode 266, which is used in step S107, is simply proportional to the input electric energy P, as indicated by equation (5). Even with this assumption, it is possible to accurately control the temperature of the first high-frequency electrode 266. In addition, in order to more accurately control the temperature of the first high-frequency electrode 266, the relationship between the input electric energy P and the temperature difference ΔT may be accurately obtained based on experiments or calculation and the temperature may be controlled by using a mathematical expression including an obtained constant term or a higher-order mathematical expression.

In this embodiment, the decision of the input power P used in step S108 is based on the simple control using equation (7), i.e., changing the input power at a rate proportional to the difference between the temperature Trp of the resistance pattern 313 and the estimated temperature Thfe of the first high-frequency electrode 266. For more accurate control, it is possible to set the power P to be input next by using a more complicated mathematical expression by, for example, introducing a differential term based on a change in the estimated temperature Thfe of the first high-frequency electrode 266 or adding a cubic term of the difference between the temperature Trp of the resistance pattern 313 and the estimated temperature Thfe of the first high-frequency electrode 266. Using a more complicated mathematical expression in this manner can set the estimated temperature Thfe of the first high-frequency electrode 266 to the set temperature Tset in a shorter period of time or suppress overshoot relative to the set temperature Tset.

In this embodiment, in each heater member 300, the resistance pattern 313 and the joining metal layer 319 joined to the first high-frequency electrode 266 are formed on the upper and lower surfaces of the substrate 311, respectively. However, the embodiment is not limited to this. For example, even if the resistance pattern 313 is formed on the upper surface of each substrate 311 having a thickness and the joining metal layer 319 is formed on a side surface of the substrate 311, since a temperature difference occurs between the temperature of the resistance pattern 313 and the temperature of the joining metal layer 319, the same technique as that described in this embodiment can be used. Each heater member 300 may have another shape. Although the temperature control method has been described by exemplifying the first high-frequency electrode 266, the same also applies to temperature control on the second high-frequency electrode 270.

[Second Embodiment]

The second embodiment of the present invention will be described next. The second embodiment will be described below with reference to differences from the first embodiment. The same reference numerals denote the same parts, and a description of them will be omitted. In the first embodiment, the temperature of the heater member 300 is obtained based on the resistance of the resistance pattern 313. In contrast to this, the second embodiment has temperature measurement resistance patterns disposed to obtain the temperatures of heater members.

Figure 11:
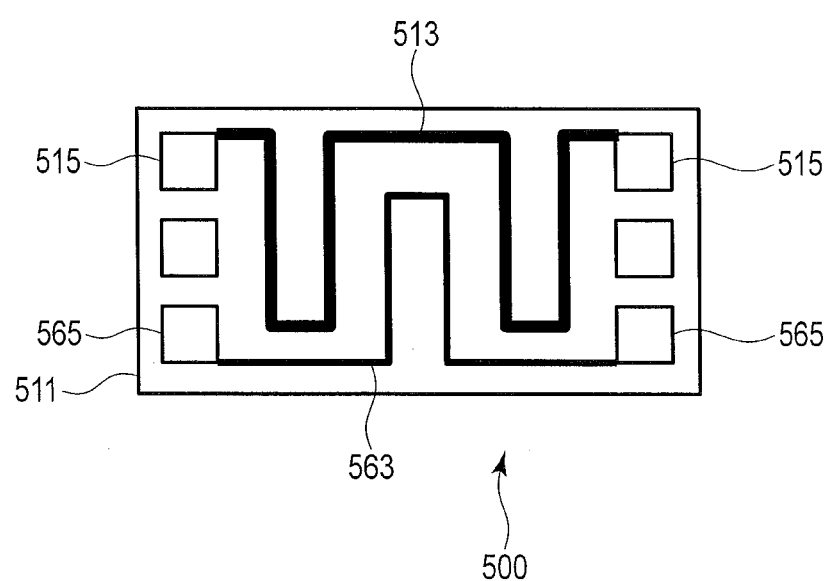
FIG. 11 is a schematic view showing an example of the arrangement of a heater member of a medical treatment system according to the second embodiment of the present invention.

FIG. 11 shows an example of the arrangement of a heater member 500 used in this embodiment. As shown in FIG. 11, like the heater member 300 according to the first embodiment, the heater member 500 has a resistance pattern 513 formed on the upper surface of a substrate 511. Electrodes 515 are formed on the two ends of the resistance pattern 513. In this embodiment, a temperature measurement resistance pattern 563 is further formed on the upper surface of the substrate 511. Electrodes 565 are formed on the two ends of the temperature measurement resistance pattern 563.

FIG. 12 shows an arrangement including a first high-frequency electrode 266, the heater members 500, a relay chip 521, connection chips 531, and wires connecting them according to the embodiment. As shown in FIG. 12, as in the first embodiment, the six heater members 500, the one relay chip 521, and the two connection chips 531 are arranged on the first high-frequency electrode 266. As shown in FIG. 11, in this embodiment, the resistance pattern 513 and the temperature measurement resistance pattern 563 are formed on each heater member 500, and, in addition, the relay chip 521 and the connection chip 531 each include two or more electrodes.

As shown in FIG. 12, a heater member conducting line 268a is connected to one electrode 539 formed on one connection chip 531 as in the first embodiment. Likewise, a heater member conducting line 268b paired with heater member conducting line 268a is connected to the one electrode 539 formed on the other connection chip 531. A temperature measurement conducting line 570a is connected to the other electrode 569 formed on the one connection chip 531. Likewise, a temperature measurement conducting line 570b is connected to the other electrode 569 formed on the other connection chip 531.

Electrodes 539 to which heater member conducting lines 268a and 268b of the connection chips 531 are connected are connected to electrodes 515 connected to the resistance patterns 513 of the adjacent heater members 500 via wires 553 formed by wire bonding. Electrodes 515 connected to the resistance patterns 513 of the heater members 500 adjacent to each other in the longitudinal direction are also connected to each other via wires 551 formed by wire bonding. At the distal end portion of the first high-frequency electrode 266, electrodes 515 of the heater members 500 facing each other through the cutter guide groove 262a are connected to each other via one electrode 525 formed on the relay chip 521.

Electrodes 569 to which the temperature measurement conducting lines 570a and 570b of the connection chips 531 are connected are connected to electrodes 565 connected to the temperature measurement resistance patterns 563 of the adjacent heater member 500 via wires 571 formed by wire bonding. Electrodes 565 connected to the temperature measurement resistance patterns 563 of the heater members 500 adjacent to each other in the longitudinal direction are connected to each other via wires 572 formed by wire bonding. Note that at the distal end portion of the first high-frequency electrode 266, electrodes 565 of the heater members 500 facing each other through the cutter guide groove 262a are connected to each other via the other electrode 575 formed on the relay chip 521.

Connecting the above components in this manner allows to apply a voltage to each resistance pattern 513 via heater member conducting lines 268a and 268b. Likewise, it is possible to apply a voltage to each temperature measurement resistance pattern 563 via the temperature measurement conducting lines 570a and 570b. That is, it is possible to independently apply voltages to the resistance pattern 513 and the temperature measurement resistance pattern 563.

Figure 13:
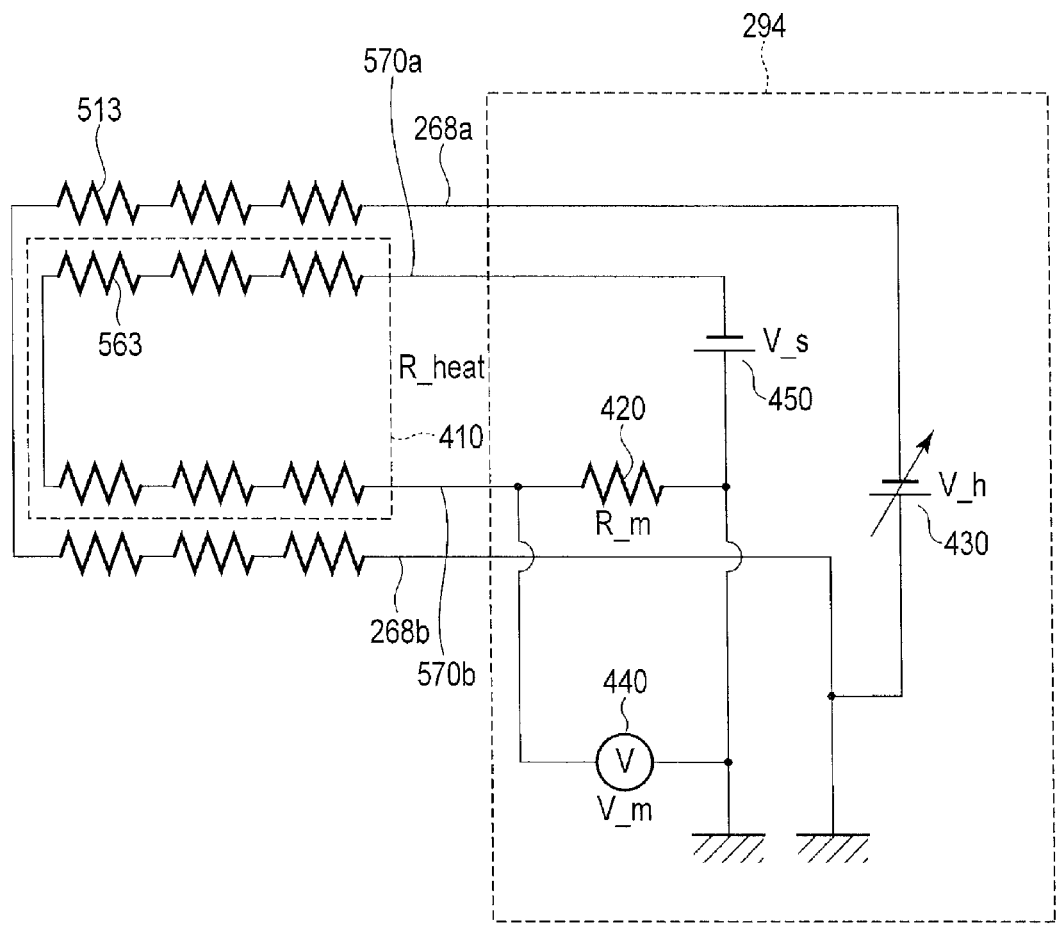
FIG. 13 is a view showing an example of the circuit configuration of a medical treatment system according to the second embodiment.

FIG. 13 shows a circuit diagram of the resistance pattern 513 and temperature measurement resistance pattern 563 of the heater member 500 and a heating element driving circuit 294. In this embodiment, a monitor resistor 420 is connected in series with the temperature measurement resistance pattern 563. As in the first embodiment, a variable voltage source 430 applies a variable voltage V_h to the resistance pattern 513. On the other hand, a fixed voltage source 450 applies a constant voltage with a voltage V_s to the temperature measurement resistance pattern 563. In this case, the power input to the temperature measurement resistance pattern 563 is very smaller than that input to the resistance pattern 513. For example, at the start of heating, a power of several hundred W is input to the resistance pattern 513 to heat the first high-frequency electrode 266 to 200° C. or more in about 5 sec. However, the power consumed by the temperature measurement resistance pattern 563 is about several W. A voltage measuring device 440 measures the potential difference between the two terminals of the monitor resistor 420. In this embodiment, the total resistance of the six temperature measurement resistance patterns 563 connected in series is represented by R_heat.

In control operation in the first embodiment described with reference to FIG. 10, using the above arrangement allows the second embodiment to perform the same control as in the first embodiment by replacing the voltage V_h with the voltage V_s and using the resistance R_heat of the temperature measurement resistance patterns 563.

In addition, this embodiment may be configured to use a constant current source as a power supply instead of the fixed voltage source 450 and measure the potential difference between the two terminals of the total resistance R_heat of the temperature measurement resistance patterns 563 by using the voltage measuring device 440. In this case, the embodiment is configured to calculate the total resistance R_heat in steps S102 to S104 based on a constant current and the potential difference between the two terminals of the total resistance R_heat. In this case as well, a medical treatment apparatus 210 functions in the same manner as in the first embodiment described with reference to FIG. 10.

The first embodiment obtains the temperature of the resistance pattern 513 by measuring the resistance of the resistance pattern 513. In contrast to this, the second embodiment obtains the temperature of the temperature measurement resistance pattern 563 by measuring the resistance of the temperature measurement resistance pattern 563. Since the resistance pattern 513 and the temperature measurement resistance pattern 563 are disposed close to each other on the same surface of the substrate 511, the temperature of the temperature measurement resistance pattern 563 can be regarded as the temperature of the resistance pattern 513.

At an early stage after the start of heating, to set the temperature of the first high-frequency electrode 266 to a set temperature Tset, it is necessary to input large power to the resistance pattern 513. On the other hand, after the temperature of the first high-frequency electrode 266 is set to the set temperature Tset, the power to be input to the resistance pattern 513 to hold the temperature is not very large. As described above, the power to be input to the resistance pattern 513 varies in a very wide range. That is, the voltage V_h to be applied varies in a wide range. In the arrangement in which the monitor resistor 420 is connected in series with the resistance pattern 513 and the voltage measuring device 440 measures the potential difference V_m between the two terminals of the monitor resistor 420 as in the first embodiment, the potential difference V_m between the two terminals of the monitor resistor 420 varies in a wide range. In this case, it is necessary to detect a change in the potential difference V_m by a change in the resistance R_heat originating from a change in the temperature of the resistance pattern 513 while the applied voltage V_h greatly changes. For this reason, the voltage measuring device 440 is required to have high measurement accuracy. In addition, since the resistance R_heat is calculated by referring to the applied voltage V_h in step S104, an output from the variable voltage source 430 is required to have high linearity.

In contrast to this, in this embodiment, the monitor resistor 420 is connected in series with the temperature measurement resistance pattern 563, and the fixed voltage source 450 applies the constant voltage V_s to them. Therefore, the potential difference V_m between the two terminals of the monitor resistor 420 may be obtained by detecting a change in the potential difference V_m due to a change in the resistance R_heat originating from a change in the temperature of the temperature measurement resistance pattern 563, and hence it is relatively easy to perform measurement using the voltage measuring device 440. In addition, since the resistance R_heat is calculated by referring to the voltage V_s applied by the fixed voltage source 450 in step S104, the linearity of the power source hardly poses any problem. In addition, since the accuracy of the variable voltage source 430 has no influence on temperature measurement, the design of the variable voltage source 430 is free from regulation by temperature measurement. Furthermore, it is possible to perform control based on pulse width modulation instead of control using the variable voltage source 430, although a sufficiently high frequency is required. In this embodiment, the resistance pattern 513 and the temperature measurement resistance pattern 563 are formed in one heater member 500. For this reason, the first high-frequency electrode 266 of this embodiment has a simple arrangement, and hence can be manufactured at a relatively low cost.

As described above, this embodiment can implement accurate temperature control even by using the relatively inexpensive variable voltage source 430 and voltage measuring device 440. The embodiment is in particular suitable for a design that uses a large maximum input electric energy to set the temperature of the first or second high-frequency electrode 266 or 270 to a set temperature in a short period of time.

[Third Embodiment]

The third embodiment of the present invention will be described next. The third embodiment will be described below with reference to differences from the first embodiment. The same reference numbers denote the same parts, and a description of them will be omitted. The first embodiment simultaneously controls the overall first high-frequency electrode 266. However, the overall first high-frequency electrode 266 does not always uniformly come into contact with a living body tissue. That is, the first high-frequency electrode 266 can simultaneously have a portion which is in contact with the living body tissue and a portion which is not in contact with the living body tissue. In such a case, a temperature difference occurs in some place in the first high-frequency electrode 266, and hence simultaneously controlling the overall electrode may make it difficult to implement accurate temperature control. In addition, a portion of the first high-frequency electrode 266 which is not in contact with the living body tissue may become an abnormally high temperature. In this embodiment, therefore, the first high-frequency electrode 266 is divided into three zones, namely a distal end portion (zone A), an intermediate portion (zone B), and a proximal end portion (zone C), and configured to independently heat each zone.

This embodiment uses two types of heater members with different layouts. These two types of heater members each have a structure similar to that of the heater member 300 in the first embodiment. That is, a resistance pattern for a heater (heat generation) and an electrode are formed on the upper surface of an alumina substrate, and a polyimide film is formed on the substrate so as to cover them except for the electrode. A joining metal layer is formed on the entire lower surface of the substrate.

The two types of layouts of heater members will be described with reference to FIGS. 14A and 14B. As shown in FIGS. 14A and 14B, on each of heater members 3011 and 3012, three pairs of electrodes are on two end portions of the upper surface of a substrate. The three electrodes arranged side by side on one end portion (on the right side in FIG. 14A or 14B) will be referred to as electrodes 304-1, 305-1, and 306-1, respectively. In addition, the electrodes arranged side by side on the other end portion (on the left side in FIG. 14A or 14B) which respectively face electrodes 304-1, 305-1, and 306-1 will be referred to as electrodes 304-2, 305-2, and 306-2, respectively. These six electrodes are insulated from each other.

As shown in FIG. 14A, on heater member 3011, a resistance pattern 307 for a heater (heat generation) whose two ends are respectively connected to electrodes 304-1 and 304-2 is formed on the upper surface of the substrate. In addition, as shown in FIG. 14B, on heater member 3012, a resistance pattern 307 for a heater (heat generation) whose two ends are respectively connected to electrodes 305-1 and 305-2 is formed on the upper surface of the substrate.

In this embodiment, heater members are arranged on the first high-frequency electrode 266 in the following manner. As described above, the first high-frequency electrode 266 is divided into the three zones, namely the distal end portion (zone A), the intermediate portion (zone B), and the proximal end portion (zone C), as shown in FIG. 15. For the sake of descriptive convenience, the portions on the upper side of a cutter guide groove 262a in FIG. 15 will be respectively referred to as the upper end portions of zones A, B, and C, and the portions on the lower side of the cutter guide groove 262a will be respectively referred as the lower end portions of zones A, B, and C.

Heater members 3011 each are disposed on the upper and lower end portions of zones A and C. In this case, on the upper end portion of zone A and on the lower end portion of zone C, heater members 3011 each are disposed such that electrodes 304-1 and 306-1 face the proximal end side of the first high-frequency electrode 266. On the other hand, on the lower end portion of zone A and on the upper end portion of zone C, heater members 3011 each are disposed such that electrodes 304-1 and 306-1 face the distal end side of the first high-frequency electrode 266. That is, the orientation direction of heater members 3011 on the upper end portion of zone A and the lower end portion of zone C differs from that of heater members 3011 on the lower end portion of zone A and the upper end portion of zone C by 180°.

Heater members 3012 are each disposed on the upper and lower end portions of zone B. In this case, heater members 3012 each are disposed such that electrodes 304-1 and 306-1 face the proximal end side of the first high-frequency electrode 266. Alternatively, the direction of heater member 3012 may differ by 180° such that electrodes 304-1 and 306-1 face the distal end side of the first high-frequency electrode 266.

For the sake of descriptive convenience, heater member 3011 disposed on the upper end portion of zone A will be referred to as a heater member 301$a$; heater member 3012 disposed on the upper end portion of zone B, a heater member 301$c$; and heater member 3011 disposed on the upper end portion of zone C, a heater member 301$e$. In addition, heater member 3011 disposed on the lower end portion of zone A will be referred to as a heater member 301$b$; heater member 3012 disposed on the lower end portion of zone B, a heater member 301$d$; and heater member 3013 disposed on the lower end portion of zone C, a heater member 301$f$.

Connection chips 331$a$ and 331$b$ are respectively disposed on the upper and lower end portions of the proximal end of the first high-frequency electrode 266. Three electrodes, namely electrodes 339$a$, 339$c$, and 339$e$ are formed side by side on the connection chip 331$a$, the electrodes 339$a$, 339$c$, and 339$e$ being arranged from the upper end side to the lower end side in FIG. 15. Three electrodes, namely electrodes 339$f$, 339$d$, and 339$b$ are formed side by side on the connection chip 331$b$, the electrodes 339$f$, 339$d$, and 339$b$ being arranged from the upper end side to the lower end side in FIG. 15. Electrodes 339$a$, 339$b$, 339$c$, 339$d$, 339$e$, and 339$f$ each have the same configuration as that of electrode 339.

A relay chip 321 is disposed on the distal end of the first high-frequency electrode 266. Three electrodes, namely electrodes 325$ab$, 325$cd$, and 325$ef$ are formed side by side on the relay chip 321, the electrodes 325$ab$, 325$cd$, and 325$ef$ being arranged from the distal end side to the proximal end side. Electrodes 325$ab$, 325$cd$, and 325$ef$ each have the same configuration as that of electrode 325.

Heater members 301$a$, 301$b$, 301$c$, 301$d$, 301$e$, and 301$f$, the connection chips 331$a$ and 331$b$, and the relay chip 321 are joined to the first high-frequency electrode 266 by soldering.

A heater member conducting line 2681$a$ is connected to electrode 339$a$ of the connection chip 331$a$. A heater member conducting line 2681$c$ is connected to electrode 339$c$. A heater member conducting line 2681$e$ is connected to electrode 339$e$. A heater member conducting line 2681$b$ is connected to electrode 339$b$ of the connection chip 331$b$. A heater member conducting line 2681$d$ is connected to electrode 339$d$. A heater member conducting line 2681$f$ is connected to electrode 339$f$.

Electrode 339$a$ of the connection chip 331$a$ is connected to electrode 306-2 of heater member 301$e$ via a wire 353 by wire bonding. Electrodes 306-2 and 306-1 of heater member 301$e$ are connected to each other via the wire 353. In addition, electrode 306-1 of heater member 301$e$ is connected to electrode 304-1 of heater member 301$c$ via the wire 353. Electrodes 304-1 and 304-2 of heater member 301$c$ are connected to each other via the wire 353. Electrode 304-2 of heater member 301$c$ is connected to electrode 304-1 of heater member 301$a$ via the wire 353. Electrode 304-2 of heater member 301$a$ is connected to electrode 325$ab$ of the relay chip 321 via the wire 353. Electrode 304-1 of heater member 301$b$ is connected to electrode 325$ab$ of the relay chip 321 via the wire 353. Electrode 304-2 of heater member 301$b$ is connected to electrode 306-2 of heater member 301$d$ via the wire 353. Electrodes 306-2 and 306-1 of heater member 301$d$ are connected to each other via the wire 353. Electrode 306-1 of heater member 301$d$ is connected to electrode 306-2 of heater member 301$f$ via the wire 353. Electrodes 306-2 and 306-1 of heater member 301$f$ are connected to each other via the wire 353. Electrode 306-1 of heater member 301$f$ is connected to electrode 339$b$ of the connection chip 331$b$ via the wire 353.

With this connection, heater member conducting line 2681$a$, the resistance pattern 307 of heater member 301$a$, the resistance pattern 307 of heater member 301$b$, and heater member conducting line 2681$b$ are sequentially connected in series. Likewise, heater member conducting line 2681$c$, the resistance pattern 307 of heater member 301$c$, the resistance pattern 307 of heater member 301$d$, and heater member conducting line 2681$d$ are sequentially connected in series by connecting the electrodes of the connection chips, heater members, and relay chip via the wires 353 formed by wire bonding. Likewise, heater member conducting line 2681$e$, the resistance pattern 307 of heater member 301$e$, the resistance pattern 307 of heater member 301$f$, and heater member conducting line 2681$f$ are sequentially connected in series.

Heater member conducting lines 2681$a$ and 2681$b$ are connected to the energy source 214 as an external heating controller via the cable 228. In addition, heater member conducting lines 2681$c$ and 2681$d$ are connected to the energy source 214 as the external heating controller via the cable 228. Furthermore, the heater member conducting lines 2681$e$ and 2681$f$ are connected to the energy source 214 as the external heating controller via the cable 228. For connection in the energy source 214, a total of three circuits, each similar to that described with reference to FIG. 9 in the first embodiment, are arranged for the respective zones. With this arrangement, therefore, this embodiment can perform independent temperature control in each zone. Each control operation is the same as that in the first embodiment.

The above arrangement can control heater members 301$a$ and 301$b$ arranged in zone A via heater member conducting lines 2681$a$ and 2681$b$. Likewise, the arrangement can control heater members 301$c$ and 301$d$ arranged in zone B via heater member conducting lines 2681$c$ and 2681$d$. Likewise, the arrangement can control heater members 301$e$ and 301$f$ arranged in zone C via heater member conducting lines 2681$e$ and 2681$f$.

In this embodiment, the wires which connect the chips to each other are formed in the form of loops between the chips and on the chips. Performing wiring by wire bonding in this manner can form many wires in a small region. This can implement space saving. Even increasing the number of zones in this embodiment hardly makes it difficult to performing wiring.

The first embodiment cannot change input power in accordance with places on the first high-frequency electrode 266. For this reason, if part of the first high-frequency electrode 266 is in contact with a living body tissue to be heated while the other part is not in contact with the living body tissue, temperature unevenness occurs within the first high-frequency electrode 266. This may lead to difficulty in implementing accurate temperature control. In addition, only a portion which is not in contact with the living body tissue may become an abnormally high temperature. In contrast to this, this embodiment can perform temperature measurement in each zone and adjust input power in accordance with the measurement. This makes it possible to control the temperature of the first high-frequency electrode 266 with high accuracy. In addition, it is possible to prevent a portion from being heated to an abnormally high temperature. This embodiment is specifically effective when the first high-frequency electrode 266 partly comes into contact with a living body tissue. The same applies to the second high-frequency electrode 270.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of controlling a medical treatment apparatus comprising:
    a heating electric resistance pattern configured to generate heat; and
    a heat transfer surface configured to transfer the heat generated by the heating electric resistance pattern to a living body tissue to heat the living body tissue to a target temperature,
    wherein the method comprises:
        calculating a resistance value of the heating electric resistance pattern;
        calculating a temperature of the heating electric resistance pattern based on the resistance value of the heating electric resistance pattern;
        calculating an electric energy being input to the heating electric resistance pattern;
        calculating an estimated temperature of the heat transfer surface based on the temperature of the heating electric resistance pattern and the electric energy being input to the heating electric resistance pattern; and
        calculating an electric energy to be input to the heating electric resistance pattern next based on a difference between the estimated temperature of the heat transfer surface and the target temperature,
    wherein the estimated temperature of the heat transfer surface is calculated based on a difference between:
        the temperature of the heating electric resistance pattern; and
        a value obtained by multiplying the electric energy being input to the heating electric resistance pattern by a constant.

2. The method according to claim 1,
    wherein the electric energy to be input to the heating electric resistance pattern next is calculated based on a sum of:
        a value proportional to a temperature difference between the estimated temperature of the heat transfer surface and the target temperature; and
        the electric energy being input to the heating electric resistance pattern.

3. The method according to claim 1,
    wherein the electric energy to be input to the heating electric resistance pattern next is calculated based on the resistance value of the heating electric resistance pattern.

4. A method of controlling a medical treatment apparatus comprising:
    a heating electric resistance pattern configured to generate heat; and
    a heat transfer surface configured to transfer the heat generated by the heating electric resistance pattern to a living body tissue to heat the living body tissue to a target temperature,
    wherein the method comprises:
        calculating a resistance value of the heating electric resistance pattern;
        calculating a temperature of the heating electric resistance pattern based on the resistance value of the heating electric resistance pattern;
        calculating an electric energy being input to the heating electric resistance pattern;
        calculating an estimated temperature of the heat transfer surface based on the temperature of the heating electric resistance pattern and the electric energy being input to the heating electric resistance pattern; and
        calculating an electric energy to be input to the heating electric resistance pattern next based on a difference between the estimated temperature of the heat transfer surface and the target temperature,
    wherein the estimated temperature of the heat transfer surface is calculated by offsetting the temperature of the heating electric resistance pattern by an offset value which changes in accordance with the electric energy being input to the heating electric resistance pattern, and
    wherein the electric energy to be input to the heating electric resistance pattern next is calculated so as to control the temperature of the heat transfer surface to the target temperature by controlling the temperature of the heating electric resistance pattern to a temperature differing from the target temperature by the offset value.

5. The method according to claim 4,
    wherein the offset value is proportional to the electric energy being input to the heating electric resistance pattern.

* * * * *